(12) United States Patent
Eriksson et al.

(10) Patent No.: US 10,175,075 B2
(45) Date of Patent: Jan. 8, 2019

(54) MEASUREMENTS DEVICE

(71) Applicant: FMC Kongsberg Subsea AS, Kongsberg (NO)

(72) Inventors: Anders Eriksson, Göteborg (SE); Svein-Petter Hanserud, Kongsberg (NO); Truls-Martin Larsen, Oslo (NO); Arnstein Wee, Randaberg (NO)

(73) Assignee: FMC Kongsberg Subsea AS, Kongsberg (NO)

( * ) Notice: Subject to any disclaimer, the term of this patent is extended or adjusted under 35 U.S.C. 154(b) by 114 days.

(21) Appl. No.: 15/118,878

(22) PCT Filed: Jan. 29, 2015

(86) PCT No.: PCT/EP2015/051799
§ 371 (c)(1),
(2) Date: Aug. 13, 2016

(87) PCT Pub. No.: WO2015/121076
PCT Pub. Date: Aug. 20, 2015

(65) Prior Publication Data
US 2017/0052048 A1 Feb. 23, 2017

(30) Foreign Application Priority Data

Feb. 14, 2014 (NO) .................................. 20140184

(51) Int. Cl.
*G01F 1/66* (2006.01)
*G01F 1/74* (2006.01)
(Continued)

(52) U.S. Cl.
CPC ............... *G01F 1/662* (2013.01); *G01F 1/66* (2013.01); *G01F 1/74* (2013.01); *G01F 15/00* (2013.01);
(Continued)

(58) Field of Classification Search
CPC ... G01F 1/66; G01F 1/662; G01F 1/74; G01F 15/00; G01F 15/08; G01N 22/04; G01N 33/2823
(Continued)

(56) References Cited

U.S. PATENT DOCUMENTS

| 6,915,707 B2 | 7/2005 | Nyfors et al. |
| 2009/0204346 A1 | 8/2009 | Xie |

(Continued)

FOREIGN PATENT DOCUMENTS

WO    WO 2007/129897 A1    11/2007

OTHER PUBLICATIONS

J. Koselj and V.B. Bregar, "Influence of Parameters of the Flanged Open-Ended Coaxial Probe Measurement Setup on Permittivity Measurements", Journal of Microelectronic Components, Electronic Components and Materials, vol. 42, No. 1, pp. 36-42 (2012).

(Continued)

*Primary Examiner* — Benjamin R Schmitt

(57) ABSTRACT

A device for measuring properties of a fluid flow includes a pipe having a first pipe section which includes a fluid flow modifying feature for causing a liquid part of the fluid flow to form an annular layer at an inner wall of a second pipe section arranged downstream of the first pipe section, the second pipe section including a near field probe for applying a low frequency signal to the annular layer and a full volume field probe for applying a high frequency signal into the second pipe section, and a third pipe section arranged downstream of the second pipe section, the third pipe section including a resonance enabling element that together with at least the second pipe section provides a resonator which captures parts of the frequency range of the full volume field probe.

13 Claims, 6 Drawing Sheets

(51) Int. Cl.
  *G01F 15/08* (2006.01)
  *G01F 15/00* (2006.01)
  *G01N 33/28* (2006.01)
  *G01N 22/04* (2006.01)
  *G01N 22/00* (2006.01)

(52) U.S. Cl.
  CPC ............. *G01F 15/08* (2013.01); *G01N 22/04* (2013.01); *G01N 33/2823* (2013.01); *G01N 22/00* (2013.01)

(58) Field of Classification Search
  USPC ............................................. 73/29.02, 31.05
  See application file for complete search history.

(56) References Cited

U.S. PATENT DOCUMENTS

2010/0064820 A1   3/2010   David et al.
2010/0145636 A1*  6/2010   Nyfors ................... G01F 1/584
                                                       702/49

OTHER PUBLICATIONS

E. Bondet de la Bernardie, et al., "Low (10-800 MHz) and High (40 GHz) Frequency Probes Applied to Petroleum Multiphase Flow Characterization", Measurement Science and Technology 19, pp. 1-8 (2008).

K. Folgerø and T. Tjomsland, "Permittivity Measurement of Thin Liquid Layers Using Open-Ended Coaxial Probes", Measurement Science and Technology 7, pp. 1164-1173 (1996).

* cited by examiner

MEASUREMENTS DEVICE

FIELD OF THE INVENTION

The present invention concerns the field of fluid flow measurements in pipes, and more specifically a device and a method for performing such measurements.

BACKGROUND

There is currently a number of systems/solutions for measuring the properties of a fluid flow, specifically fluid flows comprising both a gas and a liquid phase. The properties of interest include salinity, water content, both total and of separate phases, the liquid/gas ratio etc. A common feature of current systems is either a high degree of complexity, or a lack of desired accuracy in the measurements. More complex systems include those commonly referred to as MPMs, i.e. multi phase meters. In these systems, the properties of a flow are measured by use of a mass flow device (e.g. Venturi), pressure and temperature transmitters, density sensor and electromagnetic sensor. The less complex, but also less accurate, systems are usually without one or more of the aforementioned sensors WO 2007/129897 discloses a measuring device having a Venturi-induced annular flow for high-frequency multi-phase measurement. The disclosed measuring device and method makes use of broadband RF signals to obtain properties of the multi-phase flow, such as the dielectric constant/permittivity.

US 2009/0204346 A1 discloses a device having two probes which are mounted flush to the inner surface of a conduit in which a multi-phase fluid is flowing (cf. FIG. 1). The probes are configured to have different penetration depths such that one of the probes has a penetration depth which is greater than the depth/thickness of a liquid phase layer flowing on the inner wall of the conduit (cf. paragraph [0005]).

U.S. Pat. No. 6,915,707 B2 discloses a device for measuring the composition and the flow rate of a fluid comprising a mixture of e.g. oil and water, which device comprises a differential pressure element and a microwave resonator sensor. The microwave resonator sensor provides permittivity measurements which are used to deduce the fluid's properties. According to one embodiment, the conduit is provided with a coaxial structure that enables the resonance and supports a TEM wave mode (cf. column 9, lines 35 to 40). According to an alternative embodiment, the resonator is implemented by V-cone structure, which, according to the document, has the added benefit of breaking up any liquid film that may have formed along the inner wall of the conduit (cf. column 12, line 60 to column 13, line 13).

US 2010/0064820 A1 discloses a device for measuring a multi-phase fluid flowing through a pipe. The device comprises a first and a second coaxial probe, the ends of which are placed in contact with the fluid. The fluid is "illuminated" by the first probe with a first electromagnetic wave at a high frequency, and by the second probe with a second electromagnetic wave at a low frequency. The low frequency electromagnetic wave will penetrate deeper into the fluid than the high frequency electromagnetic wave. The admittance is measured at the interface between the fluid and the two probes, respectively, and by means of the measured admittances, properties of the fluid is deduced.

WO 2007/129897 A1 discloses a measuring device for determining the flow rates of a fluid comprising a multi-component mixture of a gas and at least one liquid in a pipe. The device comprises conditioning means for creating a symmetrical annular gas concentration flow condition in the pipe, and means for determining the density distribution and/or dielectric constant distribution with a cross-section of the pipe, e.g. a device for performing tomographic measurements.

Folgero and Tjomsland, "*Permittivity measurement of thin liquid layers using open-ended coaxial probes*", Meas. Sci. Technol. (1996), 1164-1173, discloses a method of using a open-ended coaxial probe for measuring the permittivity of thin liquid layers.

Based on the prior art there remains a need for a fluid water void fraction measuring device, which is both simple and robust, while at the same time may provide highly accurate measurements of a fluid flow in a pipe.

The aim of the present invention is to provide a device for measuring properties of a fluid flow in a pipe, which alleviates or avoids at least some of the disadvantages of the prior art systems.

SUMMARY OF THE INVENTION

The present invention provides a device for measuring the properties of a fluid flow in a pipe. Specifically, the device is suitable for fluids comprising both a gas phase and a liquid phase. The fluid may for instance be a product stream from a gas well, wherein the product stream comprises gas (lower hydrocarbons, such as methane, ethane and propane), condensate (higher hydrocarbons) and water. The device according to the invention is able to separate the gas phase (i.e. lower hydrocarbons) and the liquid phase (condensate or higher hydrocarbons), and by combining the use of low frequency measurements of the liquid phase with the use of high frequency measurements of the fluid, relevant properties of the fluid flow is decided/calculated. The relevant properties include salinity, water content and thickness/amount of the liquid annular phase, as well as the water content of the gas phase. A device and a method according to the invention are further defined in the appended claims, and in the following:

In one embodiment, the invention concerns a device for measuring properties of a fluid flow in a pipe, comprising a first, second and third pipe section, and where the first pipe section comprises a fluid flow modifying feature arranged such that, during use, a liquid part of the fluid flow will form an annular layer at an inner wall of the second pipe section, and the second pipe section is arranged downstream of the first pipe section and comprises at least one near field probe having a first frequency range, and at least one full volume field probe having a second frequency range, the upper limit of the first frequency range being lower than the lower limit of the second frequency range;

the third pipe section is arranged downstream of the second pipe section and comprises a resonance enabling element, such that said element and at least the second pipe section provides a resonator able to capture parts of the frequency range of the full volume field probe.

In one aspect of the device according to the invention, the first frequency range comprises at least parts of the range ~DC to 600 MHz, preferably parts of the range from 10 MHz to 600 MHz, or from 100 MHz to 500 MHz, and the second frequency range comprises at least parts of the range from 0.5 GHz to 4.0 GHz, preferably parts of the range from 0.8 GHz to 3.0 GHz, or from 1.2 GHz to 2.5 GHz.

In one aspect, the device according to the invention comprises two near field probes, each probe having a different penetration depth.

The penetration depth is with regard to how far into the annular liquid flow a fringing field from a near field probe will reach. In many types of near field probes, the penetration depth is depending on the physical size of a probe conductor. For instance, in case of a coaxial probe, the penetration depth is dependent on the diameter of the probe conductors.

In a further aspect of the device according to the invention, the fluid flow modifying feature of the first pipe section is an inner diameter which is restricted compared to an inner diameter of the second pipe section, such that a Venturi-effect is obtained during use, i.e. a liquid part of the fluid flow will form an annular layer at an inner wall of the second pipe section during use.

In a further aspect of the device according to the invention, the resonance enabling element comprises a restriction of the inner diameter of at least parts of the third pipe section, the restriction being such that said inner diameter is less than the inner diameter of the second pipe section.

In another aspect of the device according to the invention, the third pipe section is arranged downstream of the second pipe section and comprises a resonance enabling element, such that said element, the second pipe section and at least parts of the first pipe section provides a resonator able to capture parts of the frequency range of the full volume field probe.

In another aspect of the device according to the invention, the resonance enabling element comprises an annular flange at an inner wall of the third pipe section.

In another aspect of the device according to the invention, the resonance enabling element comprises an annular inlay at the inner wall of the third pipe section and the second pipe section, wherein the inlay is made in an electrically insulating material, such as glass or ceramics, and preferably arranged flush with said inner wall, and the full volume field probe is arranged within the inlay, preferably flush with an inner or outer circumference of the inlay.

In another aspect of the device according to the invention, the at least one near field probe, and/or the at least one full volume field probe, has a front end surface being flush, or coplanar, with an inner wall of the second pipe section.

In another embodiment, the invention concerns a near field probe, for a device according to the invention, comprising
  a first probe conductor,
  a dielectric insulator arranged outside of the first probe conductor, and
  a second probe conductor arranged outside of the dielectric insulator,
  a first, open-ended terminal arranged such that, during use, the probe conductors may be exposed to an annular liquid phase in a pipe; and
  wherein the first open-ended terminal is part of a front end surface which may be arranged flush with an inner wall of a pipe.

In yet another embodiment, the invention concerns a method for measuring the properties of a multi-phase fluid flow in a pipe, the flow comprising an annular liquid phase at an inner wall of the pipe, and an axial gas phase, comprising the steps of:
  Applying a low frequency signal from a near field probe, the signal comprising at least parts of a first frequency range of from ~DC to 600 MHz, to the annular liquid phase, from a position flush with the pipe wall;
  Measuring the reflected signal (or transmitted signal, if there are at least two near field probes close to each other within the fringing field distance);
  Applying a high frequency signal from a full volume field probe, the signal comprising at least parts of a second frequency range of from 0.8 GHz to 3.0 GHz, to the fluid flow, from a position flush with the pipe wall to perform a resonance measurement;
  Obtaining a quality factor and a resonance frequency from the resonance measurement; and
  Calculating the unknown parameters, i.e. the thickness, the salinity, and the water-liquid ratio of the annular liquid phase, and the water content of the gas phase, by combining a full-wave resonance model and a near field model.

The full-wave resonance model is matched to the full-volume resonance measurement for the second frequency range using quality factor(s) and a resonance frequency/frequencies depending on how many modes are used (TE110, TE210 etc.). The near field (fringing field) model is matched to the near field measurements. Eventually, full-wave resonance model and full-volume resonance measurement, near field (fringing field) model and near-field measurements are all matched simultaneously, to solve out the unknown desired parameters.

Alternatively, the method, according to the invention, for measuring the properties of a multi-phase fluid flow in a pipe, the flow comprising an annular liquid phase at an inner wall of the pipe, and an axial gas phase, comprises the steps of:
  Applying a low frequency signal from a near field probe, the signal comprising at least parts of a first frequency range of from ~DC to 600 MHz, to the annular liquid phase, from a position flush with the pipe wall;
  Measuring the reflected signal (or transmitted signal, if there are at least two near field probes close to each other within the fringing field distance);
  Obtaining the water content and salinity of the annular liquid phase from the reflected signal (or transmitted signal, if there are at least two near field probes close to each other within the fringing field distance);
  Applying a high frequency signal from a full volume field probe, the signal comprising at least parts of a second frequency range of from 0.8 GHz to 3.0 GHz, to the fluid flow, from a position flush with the pipe wall to perform a resonance measurement;
  Obtaining a quality factor and a resonance frequency from the resonance measurement; and
  Calculating the thickness of the annular liquid phase, and the water content of the gas phase by use of a full-wave transverse model.

In the context of the present invention, a near field probe is typically characterized by its physical size being significantly smaller than the wavelengths at which it is operating at. The near field probe in this scope is a probe that for its operating frequency range only sees and senses the annular liquid layer (being typically in the order of 1 mm thick) and beyond the liquid layer typically in the order of 1 mm. The radiation from the near field probe can be assumed to be negligible or so small that it is possible to calibrate for it. In practice, the near field probe is typically a capacitive probe detecting a complex capacitance (imaginary capacitance part reflects electrical loss).

In the context of the present invention, the full volume field probe for full-volume resonance must have a non-zero radiation capability (even though the radiation, and thus the physical size, may be very small relative the wave-length), but in a transmission configuration, the physically small (i.e. weak radiating) probes may still be applicable, since a clear well defined transmission resonance peak may very well be obtained—even though at an attenuated level. It may be advantageous having such small probe for full-volume resonance detection, since the presence of the probe perturb the ideal resonator (unloaded Q-factor and resonance frequency) to a minimum extent. With such a small probe, it is not in practice possible to measure full-volume resonance by reflection measurement, but only by transmission detection.

DETAILED DESCRIPTION OF THE INVENTION

Figure 1:
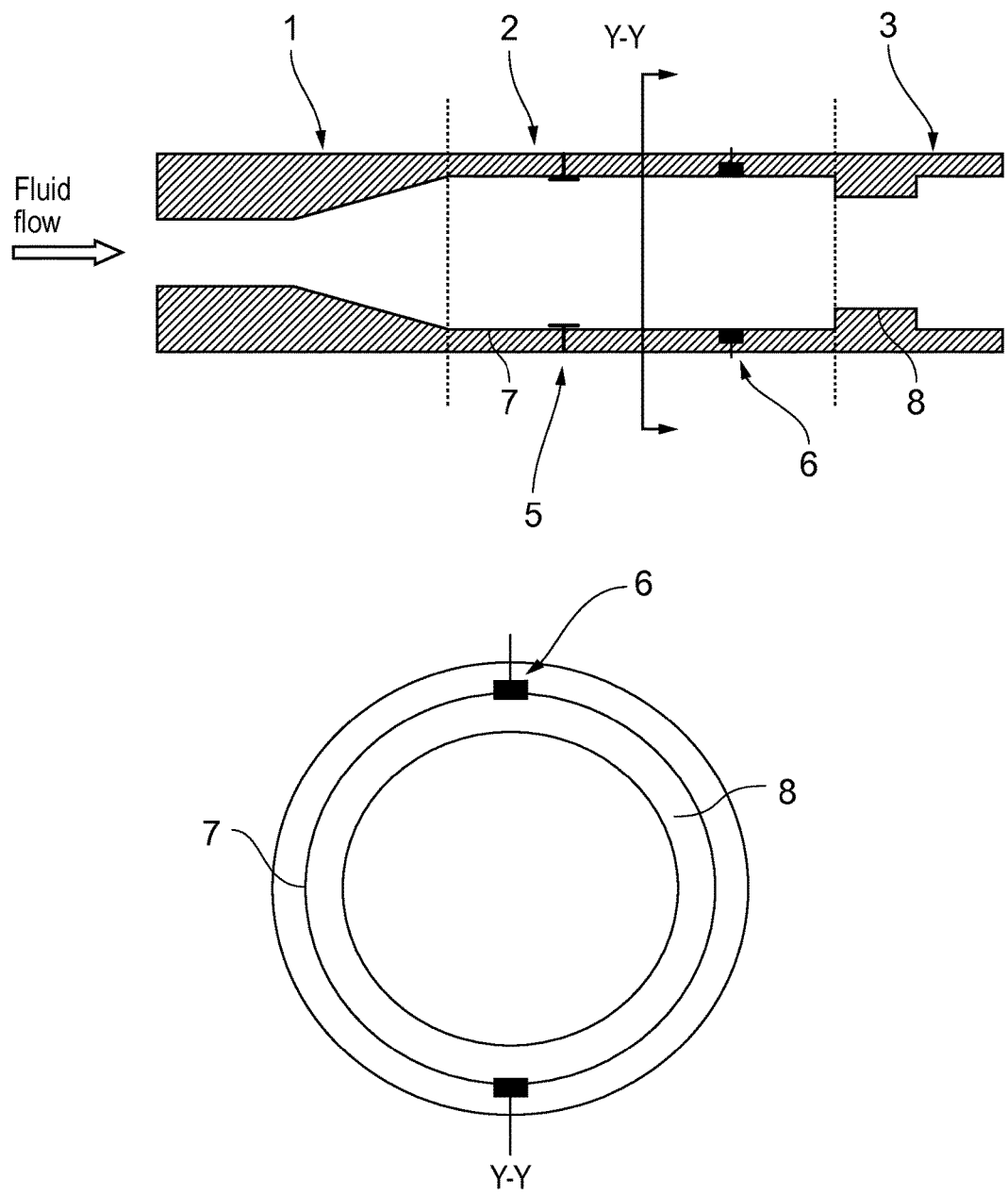
FIG. 1 shows a longitudinal cross sectional view of one embodiment of a measuring device according to the invention, and a transverse cross sectional view of same.
Figure 2:
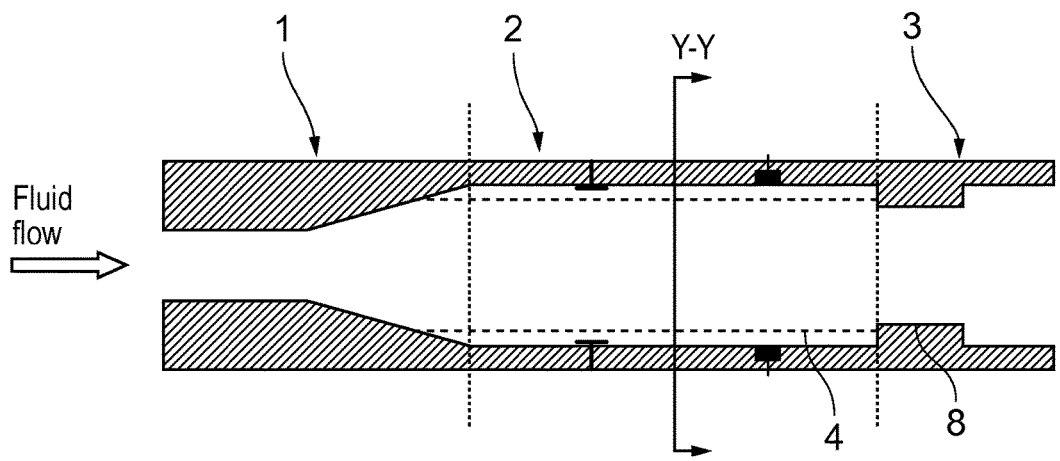
FIG. 2 shows the embodiment of FIG. 1, wherein an annular condensate layer is formed.
Figure 2:
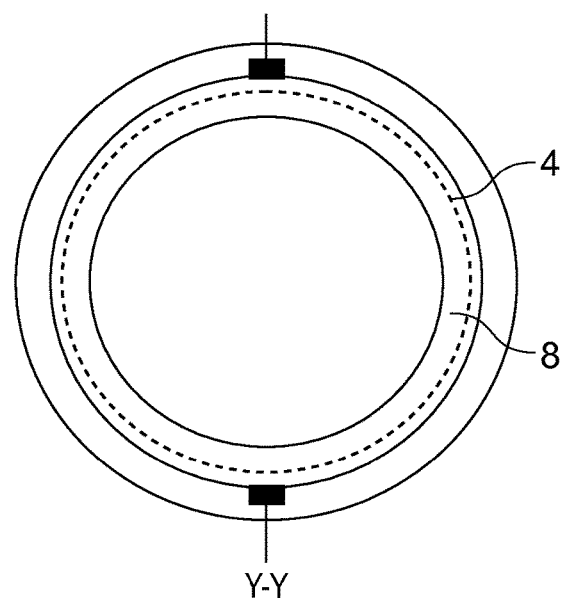

A water cut and salinity sensor (WSI), i.e. a measuring device according to the invention is shown in FIG. 1. The device comprises three pipe sections, a first pipe section 1, a second pipe section 2, and a third pipe section 3. The dotted vertical lines in FIGS. 1 and 2 are intended to only indicate the extent of each pipe section. The broad arrow indicates the direction with which a fluid flow enters the device. The device is especially suitable for multiphase flows comprising both a liquid and a gaseous component. The first pipe section 1 has a restricted inner diameter, compared to the inner diameter 7 of the second pipe section 2, and provides a Venturi-effect to the incoming fluid flow. The Venturi-effect causes the fluid flow to separate into an annular liquid phase 4 along the inner wall of the second pipe section, see FIG. 2, and a gaseous phase along the central axis of said second pipe section. To obtain the desired annular liquid phase 4 during use, the measuring device is preferably arranged such that its centerline is in a substantially vertical direction. The second pipe section 2 further comprises multiple probes 5,6 for transmitting/measuring electromagnetic radiation (EMR). In the present embodiment, the second pipe section comprises two near field probes 5 for low frequency EMR, in the present invention these frequencies are typically between ~10 MHz up to ~600 MHz, and two full volume field probes 6 for high frequency EMR, i.e. microwaves. In the present invention, the frequencies of the high-frequency probes 6 are from about 0.5 GHz to about 4.0 GHz, and typically from about 1.2 GHz to about 2.5 GHz. In this particular embodiment, the probes are able to function as both a receiver and a transmitter, but embodiments having separate probes for receiving and transmitting, respectfully, are also envisioned. For instance, high frequency TE110 and TE210 resonances are typically measured as transmission from one probe antenna to another. TEnml modes, where n>m (n is angular field variation index), have the property that the electrical field is more reduced in the center region of the resonator pipe. This makes the TE210 mode more sensitive to variations of liquid layer on an inner resonator pipe than the TE110 mode, which has a more homogeneous field distribution. Thus, for tomographic capability, it is suitable to use resonance modes that have different field strengths in different parts of the volume to be reconstructed, so that maximum unknowns can be solved out. This is in analogy with the near-field probes having different physical size and thus different electric field penetration depth.

Figure 3:
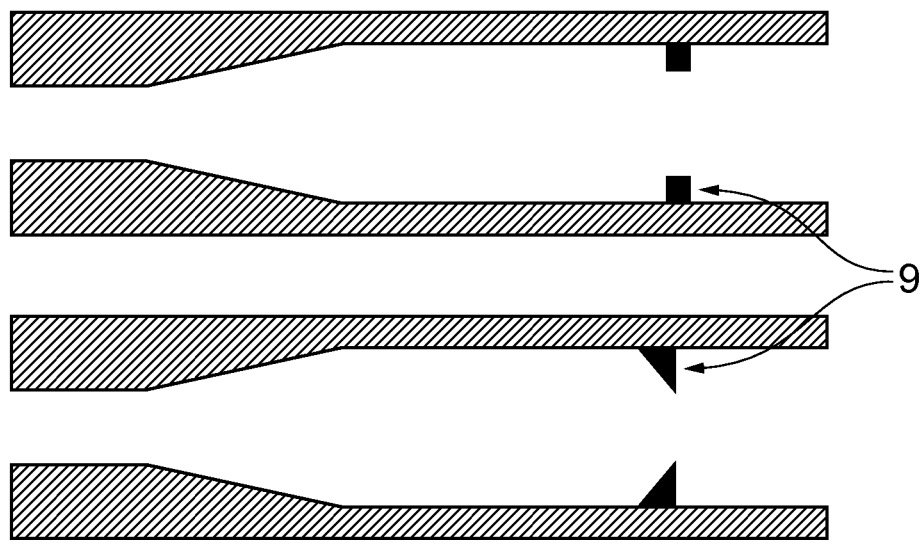
FIG. 3 shows two embodiments of a measuring device according to the invention.
Figure 4:
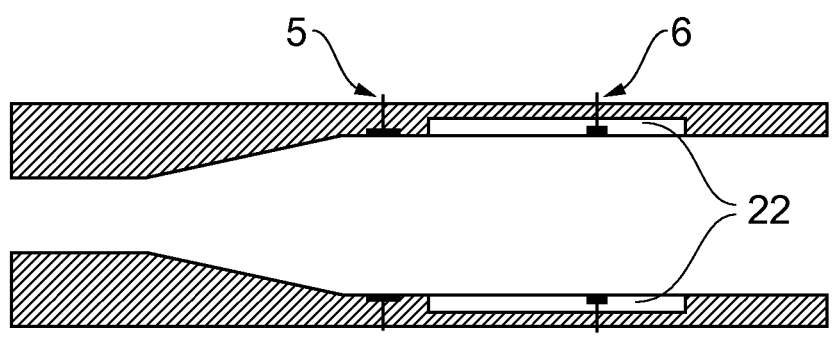
FIG. 4 shows a further embodiment of a measuring device according to the invention.
Figures 5, 6:
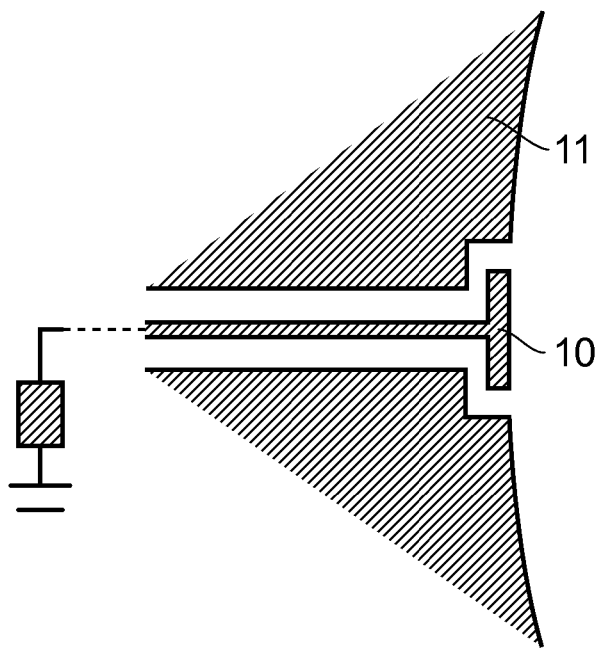
FIG. 5 shows a probe suitable for use in the embodiments of FIGS. 1-4.
FIG. 6 shows an illustration of how analytical expressions of a full-wave transverse resonance model are applied to a concentric cylindrical geometry.

The front end of the probes is designed such that they are flush, or coplanar, with the inner wall of the second pipe section, see FIG. 5. The third pipe section 3 comprises a resonance enabling element 8. The restricted inner diameter of the first pipe section 1 and the resonance enabling element 8 forms two ends of a resonance chamber, or cavity, able to capture a part of the electromagnetic energy, transmitted by the high frequency probe 6, at a certain resonance frequency. The resonance enabling element 8 may be any means which provides an annular obstacle having an inner diameter which is less than the inner diameter of the second pipe section 2. Such means may be, for instance, a restriction of the inner diameter of at least parts of the third pipe section, as shown in FIGS. 1 and 2, or an annular flange 9 at an inner wall of the third pipe section, see FIG. 3. As shown in FIG. 3, the cross-section of the annular flange 9 may vary as long as the required resonance is achieved, but is preferably designed such that the fluid flow experiences a minimal pressure drop and turbulence. It is noted that a high frequency resonator (or resonance chamber), having e.g. TE resonance modes, may be realized in at least two ways. One way, as described herein above, is having a pipe with a Venturi (pipe section 1) upstream and a reflector (flange 9 of pipe section 3) downstream of a middle measuring section (pipe section 2) to capture high frequency resonances (e.g. TE modes). Another way to realize a high frequency resonator, without a reflector, is by having an electrically insulating ceramics/glass (or other dielectrics material) annular inlay 22 (so that the WSI becomes perfectly "flush" with no narrowing of inner WSI diameter except the upstream Venturi), see FIG. 4. This annular inlay 22 permits resonances to be accommodated without becoming evanescent, since the outer inlay diameter is >the metal pipe inner diameter. Also, the electric permittivity in the glass/ceramics inlay is >the electric permittivity of air, which further more makes the resonances attaining a high Q-factor. When using this glass/ceramics inlay 22, the Venturi is only necessary for obtaining a good annular liquid-phase flow, but not necessary for obtaining high frequency resonances. Thus, when using such an inlay, the Venturi may be replaced by any element able to separate a multi-phase flow into a flow having an annular liquid-phase flow and a substantially gaseous axial flow. Such elements include various types of swirl elements, often used in subsea separators, and are well known to the skilled person. An important feature when using an annular inlay is that the full volume field probe 6 must be arranged within the pipe section covered by the inlay, otherwise the resonances would not be measured. The full volume field probe/probes may for instance be flush with the inner circumference of the inlay, or with the inlay/pipe interface. An advantage by having the full volume field probe flush with the inner circumference of the inlay is that the probe is never physically exposed to the fluid flow. The near field probe/probes may be arranged either before or after the inlay, or flush with the inner circumference of the inlay.

Figure 8:
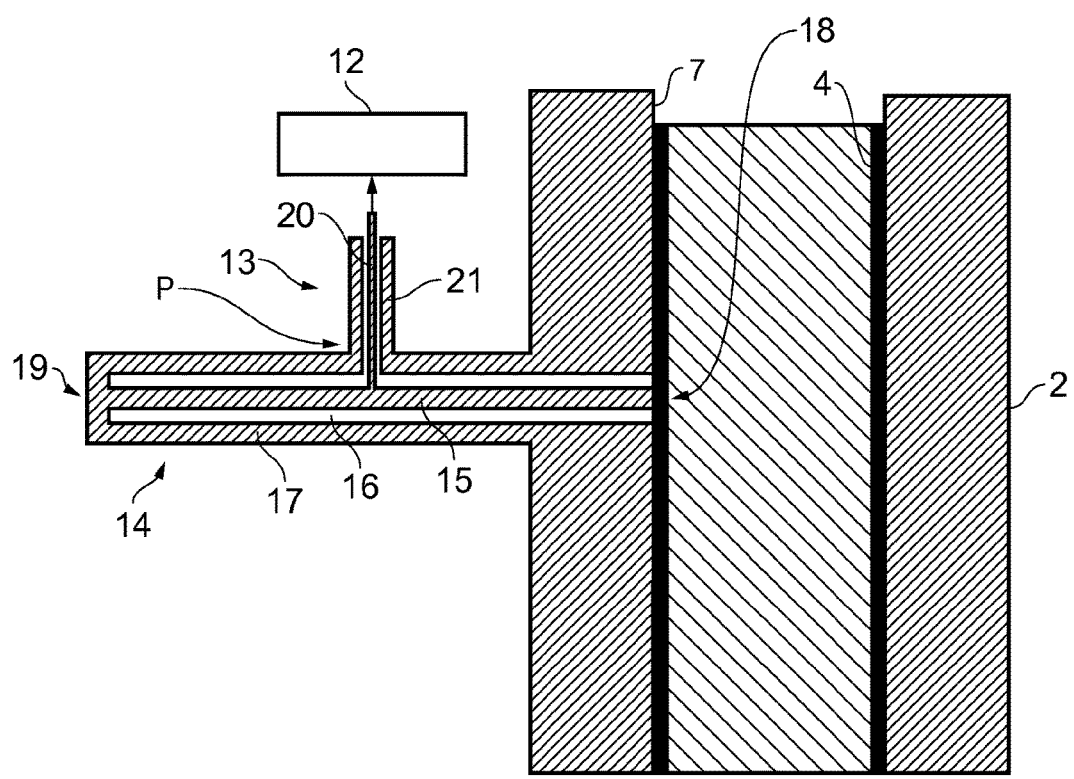
FIG. 8 shows a quarter-wave open ended coax resonator suitable for use as a near field probe.

A probe suitable for use in the present device is shown in FIG. 5. Such a probe is suitable as a near field probe or a full volume field probe. The front end 10, or first terminal (ref FIG. 8), of the probe is designed to be flush with an inner wall 11 of a pipe. Due to the design of the front end 10, the probe does not interfere with the fluid flow regime. This feature enables unperturbed near-field measurements to be made, which increases the overall accuracy. Another advantage of having coplanar, or flush, probes is that erosion problems and need of recalibration of the probe is largely reduced since the probe shape is as good as intact even though it has been eroded, thus providing a very robust solution.

Advantageously, the probe may be a Quarter-wave open ended coax resonator 14. A schematic drawing of such a probe is disclosed in FIG. 8. The probe 14 is depicted in connection with a pipe 2 (i.e. the second pipe section) having an annular liquid phase 4 and is mounted to the pipe for measuring signals indicative of at least one physical property of said layer, e.g. water content and salinity.

The probe is connected to a sensor 12 for interpreting the signals to determine the at least one parameter, and a signal line 13 for conveying the signals from the coaxial probe to the sensor 12. Sensors 12 are known as such and will not be disclosed in any detail here. However, as is known in the art, it may be advantageous to provide the sensor with a processing unit, e.g. a central processing unit (CPU), to implement the interpretation of the signals. Furthermore, or alternatively, it may be advantageous to provide the sensor with a storage unit, such as a non-volatile memory, and/or a display unit, such as a screen, to store and present the signals, respectively. Also, it may be advantageous to provide the sensor with input and output means to enable communication between the sensor 12 and other equipment, e.g. further signal processing means.

The coaxial probe 14 comprises a first, axial probe conductor 15, a dielectric insulator 16, which is arranged outside of the first probe conductor 15, and a second, cylindrical probe conductor 17, which is arranged outside of the dielectric insulator 16. Consequently, the first conductor 15, the insulator 16 and the second conductor 17 have a coaxial relationship.

The probe 14 extends through the pipe 2 and comprises a first, open-ended terminal 18 where the probe conductors 15, 17 are exposed to the annular liquid phase 4 when in operation. At the first terminal 18, the conductors 15, 17 and the insulator 16 may advantageously be arranged coplanar with the inside wall of the pipe 2 such that the probe 14 does not disturb the annular liquid phase 4 and, in addition, is not eroded by the liquid phase. Alternatively, the probe 14 may extend beyond the inside wall such that the first terminal 18 extends a predetermined distance, e.g. 1-3 mm, from the wall. The probe 14 also comprises a second, short-circuited terminal 19, where the first probe conductor 15 and the second probe conductor 17 are electrically connected to each other.

The signal line 13 is connected to the probe 14 at a predetermined position P between the first terminal 18 and the second terminal 19, which position defines a measurement reference plane. Consequently, the probe 14 acts as an open-ended quarter-wave resonator.

The signal line 13 comprises a first signal line conductor 20 which is connected to the first probe conductor 15 and a second signal line conductor 21 which is connected to the second probe conductor 17.

The measuring device according to the invention is able to measure water-volume fractions of up to at least 5.6% with salinity in this water cut of up to at least 25.47% (which is the maximum salinity of MPM multiphase instrument capability).

The basic principle behind the invention is based on electrical measurements of the fluid flow after said flow has passed the first pipe section as described above and formed an annular condensate layer at the inner wall of the second pipe section. The principle comprises the two following main steps:

1) Using a low frequency near field probe—typically a reflection measurement sensor detecting magnitude and phase (see FIG. 5). The low frequency near field probe may also be a quarter-wave open ended coax resonator designed for only detecting magnitude of transmitted (or reflected) RF signal and resonance frequency (peak (s)) of transmitted or reflected signal. In that case, detecting the phase is not required since the resonator can be used to extract both resonance frequency and Q-factor, or just a magnitude reflected (or transmitted, if there are at least two near field probes close to each other within the fringing field distance) spectrum. The front end of the low frequency near field probe is preferably coplanar, or flush, with the inner wall of the second pipe section and measures frequencies of at least parts of the range from ~DC up to ~600 MHz. The probe measures and characterizes the annular condensate layer with respect to water content and salinity (but not necessary the condensate layer thickness). This procedure can be done using "look-up" tables based on measurements or a "full-wave" model valid for a coplanar probe looking into an annular flow. It is noted that the principle of the low frequency probe measurement is as follows: for a certain upper frequency, the probe will not see through the condensate layer (when said layer is thick enough), and the measurements below this frequency is independent of the condensate thickness (enabling extraction of data for the salinity and water content). Above this frequency, the probe sees through the condensate layer—i.e. the probe measurements no longer measures only the response of the condensate layer but also the response of the wet-gas (at such frequency, where the near-field probe starts to radiate, the physical size of the near-field probe is no longer small compared to the wave-length). To a certain extent (with low accuracy) the condensate thickness can also be obtained, and all these "a-priori" data is transferred to step 2).

2) Using a high frequency full volume field probe—being a reflection or preferably transmission measurement probe detecting the magnitude of the signal (see FIG. 4). As for the low frequency probe, the front end of the probe is preferably coplanar, or flush, with the inner wall of the second pipe section. The high frequency probe transmits and measures frequencies in at least parts of the range from about 0.5 GHz to about 4.0 GHz. The probe performs a high frequency resonance measurement (either by reflection or transmission measurement of the magnitude of the signal)—measuring the quality (Q or $Q_o$) factor and resonance frequency. The resonance frequency is mainly depending on water content, whereas the Q-factor is mainly depending on salinity (this is the case for "high" salinity levels—otherwise the Q-factor is also depending on metal loss and radiation out from the full-volume resonator). Since the salinity, as well as the water content in the condensate film, is already known from step 1), the remaining unknowns are the condensate thickness and the water content in the wet-gas itself. These unknowns can be extracted from the resonance measurement using the measured Q-factor and resonance frequency. A full-wave transverse model for cylindrical concentric layers, see herein below, can be used in the extraction of data for condensate layer thickness and water content in the wet gas. In this regard, it is noted that the resonance effect (obtaining a radial standing wave at microwave frequencies) is enabled by the restricted inner diameter of the first pipe section providing a Venturi-effect and the downstream resonance enabling element of the third pipe section (for instance a restricted inner diameter of the third pipe section), see FIGS. 1-3. The restricted inner diameter of the first pipe section and the resonance enabling element of the third pipe section acts as obstacles, forming a resonance chamber, so that the electromagnetic energy, transmitted by the high frequency probe, is captured at a resonance frequency—the resonance frequency determined by the inner physical dimension of the second pipe section and the content in concentric layers/volumes inside said pipe section.

Alternatively, if near field model 1) and full wave—full volume model 2) are models containing analytical expression of electrical permittivities for condensate layer and gas, the entire problem can be solved simultaneously using models in a functional that is minimized in order to solve out all unknowns (salinity, condensate layer thickness and water content etc.).

A Full-Wave Transverse Resonance Model

The relevant properties of the fluid flow may be obtained from the data obtained in step 1 and 2 above by use of a full-wave transverse resonance model. This is an efficient and compact model with two analytical closed form expressions, see eq. 1 and eq. 2 below, that numerically are matched together to get numerical values. Input and output impedances are added at the liquid-gas interface (i.e. added just where liquid and gas meets. Note however that first, resonance frequency and Q-factor are measured, and then given as argument into the transverse resonance algorithm, and then other unknowns can be extracted) and the resonance frequency is the frequency where the sum is minimized, see eq. 3. The mathematical functions involved are Bessel and Hankel functions and the arguments to the expressions below are fundamental physical/electrical properties such as electric complex permittivity $\varepsilon$ (of mixed water-gas condensate as well as wet gas), frequency $\omega$, pipe inner radius $r_0$ and condensate thickness (condensate thickness is not directly taken as argument, but this thickness is the difference between the inner radius of the pipe and the radius from the center of the pipe to the top-surface of the condensate layer). See FIG. 6 for an illustration of how the analytical expressions are applied to a concentric cylindrical geometry.

expressions for TE (transverse electrical) resonances    Equation 1

$$Z_{out}(d) = $$

$$B \frac{e^{2iv_n(-d)} H_m^{(1)\prime}(v_n'(r_0-d))(H_m^{(2)}(v_n'r_0)Z_L - BH_m^{(2)\prime}(v_n'r_0)) + H_m^{(2)\prime}(v_n'(r_0-d))(BH_m^{(1)\prime}(v_n'r_0) - Z_L H_m^{(1)}(v_n'r_0))}{e^{2iv_n(-d)} H_m^{(1)\prime}(v_n'(r_0-d))(H_m^{(2)}(v_n'r_0)Z_L - BH_m^{(2)\prime}(v_n'r_0)) + H_m^{(2)\prime}(v_n'(r_0-d))(BH_m^{(1)\prime}(v_n'r_0) - Z_L H_m^{(1)}(v_n'r_0))}$$

-continued $$Z_{in}(r) = A \frac{J_m'(v_n r)}{J_m(v_n r)}, \text{ where } B = j\frac{\omega\mu}{v_n'} = j\sqrt{\frac{\mu}{\varepsilon}},$$

$r_0$ is pipe inner-radius, d is liquid layer thickness, and $Z_L$ is outermost load impedance (=0 for a perfect conductor). Note that $Z_{out}$ (d) can be calculated recursively through out any number of concentric layers, as well as metals with finite electric conductivity expressions for TM (transverse magnetic) resonances    Equation 2

$$Z_{out}(r) = A \frac{H_m^{(2)}(v_n r)(H_m^{(1)\prime}(v_n r_0)Z_L - AH_m^{(1)}(v_n r_0)) - (H_m^{(2)\prime}(v_n r_0)Z_L - AH_m^{(2)}(v_n r_0))H_m^{(1)}(v_n r)}{H_m^{(2)\prime}(v_n r)(H_m^{(1)\prime}(v_n r_0)Z_L - AH_m^{(1)}(v_n r_0)) - (H_m^{(2)\prime}(v_n r_0)Z_L - AH_m^{(2)}(v_n r_0))H_m^{(1)\prime}(v_n r)}$$

$$Z_{in}(r) = A \frac{J_m(v_n r)}{J_m'(v_n r)}, \text{ where } A = \frac{jv_n}{\varepsilon k} = j\sqrt{\frac{\mu}{\varepsilon}}$$

Equation 3: expressions for complex resonance frequency and quality factor

The complex resonance frequency is obtained by minimizing:

$$Z_{in}(r) + Z_{out}(r) = 0$$

then $$v_n = \omega\sqrt{\mu_0\mu_r\varepsilon_0\varepsilon_r}, \; Q_0 = \frac{\omega_{0real}}{2\omega_{0imag}}$$

Figure 7:
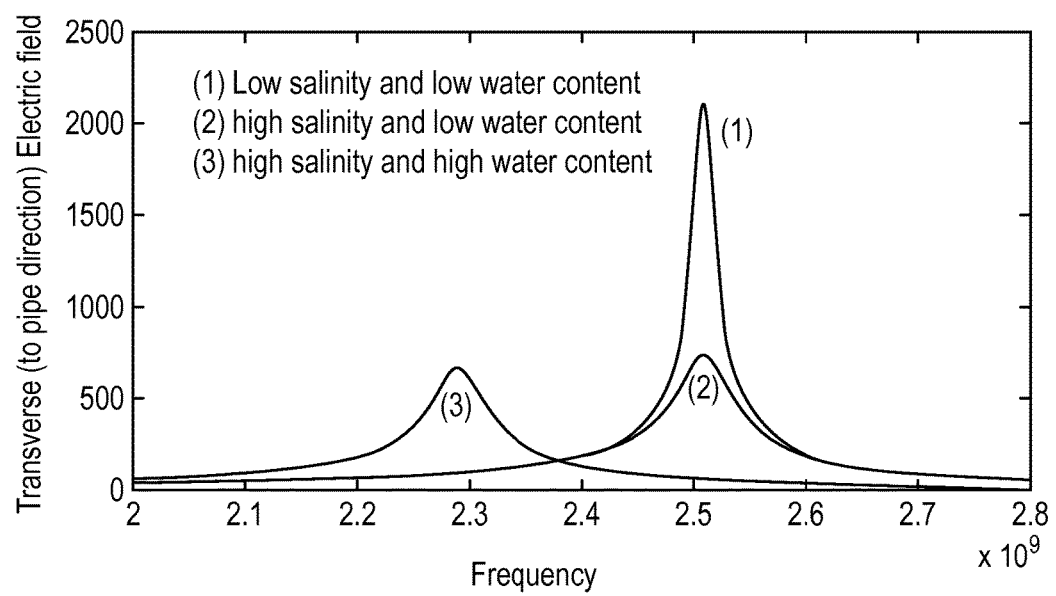
FIG. 7 shows a typical theoretical response based on simulations of a full wave resonance.

A typical theoretical response based on simulations of the full wave resonance is shown in FIG. 7. The peaks 1-3, show that the resonance frequency $$f_0 \sim \frac{1}{\sqrt{\varepsilon_r}}$$

and the transverse electric field depend on the salinity and the water content of the fluid flow. The peak 3 indicates a fluid flow having higher water content than the fluid flows corresponding to peaks 1 and 2, thus having a lower resonance frequency. For pure water $\varepsilon_r \approx 80$, and for dry gas (lower hydrocarbons) $\varepsilon_r$ is approx. 1. Peak 1 shows a fluid flow having low salinity and low water content. The low salinity of the fluid flow causes a low electric conductivity and less electrical loss, which leads to a sharper peak, i.e. a high Quality factor. Peak 2 is corresponding to a fluid flow of high salinity. The high salinity causes higher electric conductivity and more electrical loss, which leads to a less sharp peak, i.e. a low Quality factor.

The invention claimed is:

1. A device for measuring properties of a fluid flow which comprises:
   a pipe through which the fluid is directed, the pipe comprising first, second and third pipe sections;
   the first pipe section comprising a fluid flow modifying feature arranged such that, during use, a liquid part of the fluid flow will form an annular layer at an inner wall of the second pipe section;

the second pipe section being arranged downstream of the first pipe section and comprising at least one near field probe having a first frequency range, the at least one near field probe being configured to apply a low frequency signal to the annular layer from a position flush with an inner wall of the second pipe section and to measure the reflected signal;

the second pipe section further comprising at least one full volume field probe having a second frequency range, the at least one full volume field probe being configured to apply a high frequency signal into the second pipe section from a position flush with the inner wall of the second pipe section to perform a resonance measurement and to obtain a quality factor and resonance frequency from the resonance measurement, wherein an upper limit of the first frequency range is lower than a lower limit of the second frequency range; and the third pipe section being arranged downstream of the second pipe section and comprising a resonance enabling element, such that said resonance enabling element and at least the second pipe section provide a resonator able to capture parts of the frequency range of the at least one full volume field probe.

2. The device according to claim 1, wherein the first frequency range comprises at least parts of the range from approximately 0 MHz to 600 MHz and the second frequency range comprises at least parts of the range from greater than 0.6 GHz to 4.0 GHz.

3. The device according to claim 2, wherein the first frequency range comprises at least parts of the range from 10 MHz to 600 MHz and the second frequency range comprises at least parts of the range from 0.8 GHz to 3.0 GHz.

4. The device according to claim 2, wherein the first frequency range comprises at least parts of the range from 100 MHz to 500 MHz and the second frequency range comprises at least parts of the range from 1.2 GHz to 2.5 GHz.

5. The device according to claim 1, wherein the at least one near field probe comprises two near field probes, each having a different penetration depth.

6. The device according to claim 1, wherein the fluid flow modifying feature of the first pipe section comprises an inner diameter of the first pipe section which is smaller than an inner diameter of the second pipe section such that a Venturi-effect is obtained during use.

7. The device according to claim 1, wherein the resonance enabling element comprises a restricted portion of the inner diameter of the third pipe section, the restricted portion having an inner diameter which is less than the inner diameter of the second pipe section.

8. The device according to claim 1, wherein the resonance enabling element, the second pipe section and at least part of the first pipe section provide a resonator able to capture parts of the frequency range of the at least one full volume field probe.

9. The device according to claim 1, wherein the resonance enabling element comprises an annular flange which projects radially inwardly from an inner wall of the third pipe section.

10. The device according to claim 1, wherein the resonance enabling element comprises an annular inlay in the inner wall of the third pipe section and the second pipe section, wherein the inlay is made of an electrically insulating material and is arranged flush with said inner wall, and wherein the full volume field probe is arranged within the inlay.

11. The device according to claim 1, wherein at least one of the near field probe and the full volume field probe has a front end surface which is flush with an inner wall of the second pipe section.

12. The device according to claim 1, wherein said at least one near field probe comprises:
   a first probe conductor;
   a dielectric insulator arranged outside of the first probe conductor;
   a second probe conductor arranged outside of the dielectric insulator; and
   an open-ended terminal arranged such that, during use, the first and second probe conductors are exposed to an annular liquid phase in the pipe;
   wherein the open-ended terminal is part of a front end surface of the probe which is arranged flush with the inner wall of the pipe.

13. A method of measuring the properties of a multi-phase fluid flow in a pipe, the flow comprising an annular liquid phase located at an inner wall of the pipe and a gas phase located radially inwardly of the liquid phase, the method comprising:
   applying a low frequency signal from a near field probe to the annular liquid phase from a position flush with the pipe wall, the low frequency signal comprising at least parts of the range from approximately 0 MHz to 600 MHz;
   measuring the reflected signal;
   applying a high frequency signal from a full volume field probe to the fluid flow from a position flush with the pipe wall to perform a resonance measurement, the high frequency signal comprising at least parts of the range from 0.8 GHz to 3.0 GHz;
   obtaining a quality factor and a resonance frequency from the resonance measurement; and
   calculating the thickness, the salinity, and the water-liquid ratio of the annular liquid phase and the water content of the gas phase by combining a full-wave resonance model and a near field model.

* * * * *